US00PP09589P

United States Patent [19]

Trees

[11] Patent Number: Plant 9,589

[45] Date of Patent: Jun. 18, 1996

[54] GERANIUM PLANT NAMED "BFP-864 BRIGHT LAVENDER"

[75] Inventor: Scott C. Trees, Arroyo Grande, Calif.

[73] Assignee: Geo. J. Ball, Inc., West Chicago, Ill.

[21] Appl. No.: 462,777

[22] Filed: Jun. 5, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Burns, Doane, Swecker & Mathis

[57] ABSTRACT

The new and distinct *Pelargonium×hortorum* cultivar named 'BFP-864 Bright Lavender' is provided. This new Zonal Geranium was the result of a controlled breeding program wherein the a plant designed 3841-3 (non-patented in the United States) was pollinated by the 'Fox' cultivar U.S. Plant Pat. No. 7,083). The new cultivar forms attractive semi-double lavender florets commonly with white coloration that radiates outwardly from the bases of the petals. Medium green foliage is well retained during shipment. A medium self-branching growth habit is exhibited that does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-864 Bright Lavender'.

The new cultivar is a product of a planned breeding program which had the objective of the creation of a Geranium cultivar that exhibits uniform flowers, medium green foliage, a medium self-branching growth habit that requires no growth regulator, a propensity for rapid rooting, and stable foliage coloration during shipment.

The breeding program that resulted in the production of the new cultivar of the present invention was carried out in a controlled environment during 1992 at Arroyo Grande, Calif., U.S.A. The female parent (i.e., seed parent) was a plant designated 3841-3 (non-patented in the United States) which exhibits single dark pink florets with dark green foliage. The male parent (i.e., pollen parent) was the 'Fox' cultivar (United States Plant Pat. No. 7,083) which exhibits semi-double purple florets with medium green foliage. The parentage of the new 'BFP-864 Bright Lavender' cultivar can be summarized as follows:

3841-3×'Fox'.

'BFP-864 Bright Lavender' was discovered and selected during 1992 as a highly distinctive flowering plant from among the progeny of the stated cross at Arroyo Grande, Calif., U.S.A. This plant was initially designated BFP-864.

It was found that the new cultivar of the present invention:

(a) exhibits attractive semi-double lavender florets commonly with white coloration that radiates outwardly from the bases of the petals,
(b) forms attractive medium green foliage, and
(c) exhibits a medium self-branching growth habit in the absence of a growth regulator.

When plant material of the 'BFP-864 Bright Lavender' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of the 'BFP-864 Bright Lavender' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demonstrated that the combination of unique characteristics as herein described for the 'BFP-864 Bright Lavender' cultivar is fixed and is retained through successive generations of such asexual reproduction.

The new 'BFP-864 Bright Lavender' cultivar has not been observed under all possible environmental conditions. Accordingly, the described phenotype may vary somewhat with variations in the environment, such as temperature, light intensity, and day length.

Of the many commercial cultivars, the 'BFP-721 Bright Lilac' cultivar (United States plant patent application Ser. No. 08/341,991, filed Nov. 14, 1994 ) is considered to be the most similar to the new cultivar of the present invention. When the new cultivar of the present invention is compared to the 'BFP-721 Bright Lilac' cultivar, it is found that the 'BFP-864 Bright Lavender' cultivar exhibits a less compact growth habit (e.g., approximately 27 to 33 cm. in height vs. approximately 26 to 28 cm.), smaller florets (e.g., approximately 4.2 to 4.4 cm. vs. approximately 4.5 to 5.0 cm. in diameter), and larger leaves (e.g., approximately 9.0 to 10.0× approximately 7.6 to 8.5 cm. vs. approximately 8.0 to 9.0 cm.×approximately 7.0 to 7.5 cm.). The 'BFP-864 Bright Lavender' cultivar additionally exhibits longer pedicels, and fewer florets per umbel as specified in greater detail hereafter.

The new cultivar of the present invention is being marketed by Geo. J. Ball, Inc. under the Satisfaction trademark.

BRIEF DESCRIPTION OF THE PHOTOGRAPH

The accompanying photograph of FIG. 1 shows the general appearance of an overall plant of the new 'BFP-864 Bright Lavender' cultivar with colors being as nearly true as it is reasonably possible to make the same in a color illustration of this character. The plant was being grown in a greenhouse at West Chicago, Ill., U.S.A.

DETAILED DESCRIPTION

Figure 1:
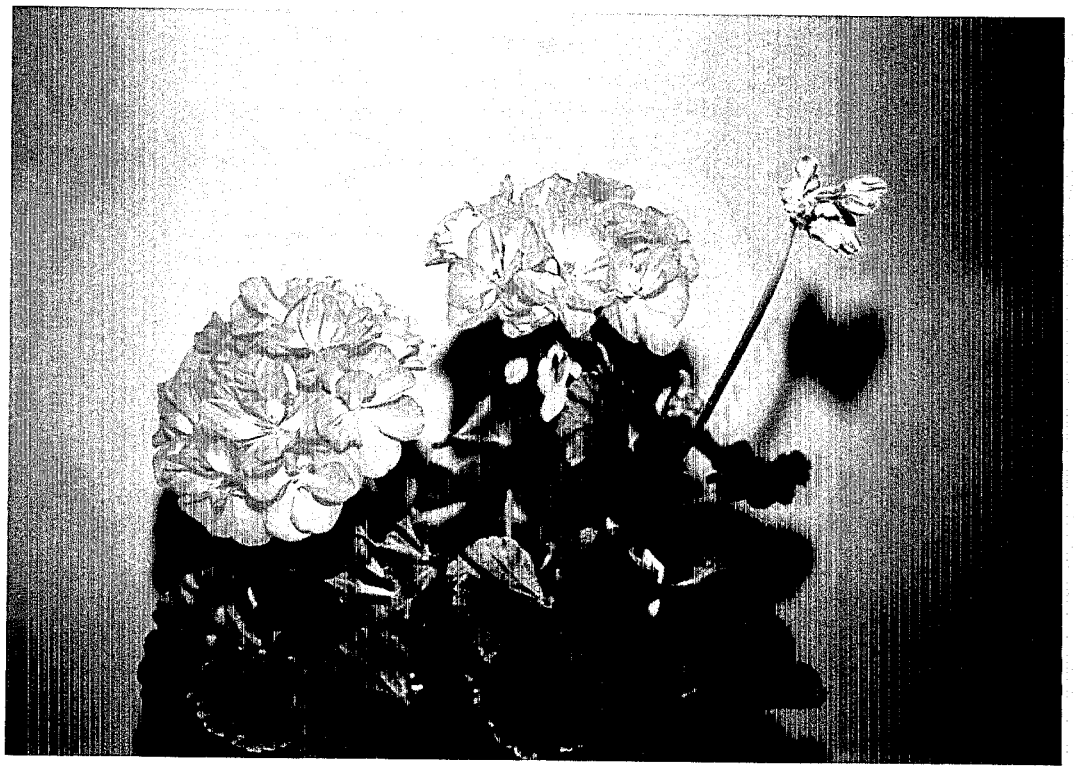

The following observations, measurements and comparisons describe plants grown in Ball FloraPlant's greenhouses located at West Chicato, Ill., U.S.A., under conditions which approximate those generally used in commercial practice. In the following description, color references are made to The R.H.S. Colour Chart of The Royal Horicultural Society, London, England. The color values were determined between 11:00 and 11:45 a.m. on Jan. 3, 1995, under natural light conditions of 2,000 footcandles.

Classification:

*Botanical.*—*Pelargonium×hortorum* Bailey, cv. 'BFP-864 Bright Lavender'.

*Commercial.*—Zonal geranium.

Inflorescence

A. Umbel:

*Average diameter.*—Approximately 7.5 to 9.5 cm. compared to approximately 8.5 to 9.0 cm. for the 'BFP-721 Bright Lilac' cultivar.

*Average depth.*—Approximately 6.0 to 8.0 cm. compared to approximately 7.0 to 9.0 cm. for the 'BFP-721 Bright Lilac' cultivar.

*Peduncle length.*—Approximately 18.0 to 4.0 cm. compared to approximately 15.0 to 17.0 cm. for the 'BFP-721 Bright Lilac' cultivar.

*Pedicel length.*—Approximately 3.5 to 2.5 to compared to approximately 2.5 to 3.2 cm. for the 'BFP-721 Bright Lilac' cultivar.

*Number of umbels plant.*—When grown in a 10 cm. pot at 9 weeks after the sticking of a rooted cutting, there commonly are aproximately 4 to 5 umbels per plant. The 'BFP-721 Bright Lilac' cultivar commonly forms approximately 4 to 6 umbels per plant.

*Number of florets umbel.*—When grown in 10 cm. pots at 9 weeks, approximately 33 to 38 florets per umbel commonly are formed. This compares to approximately 45 to 50 florets per umbel for the 'BFP-721 Bright Lilac' cultivar.

B. Corolla:

*Average diameter.*—Approximately 4.2 to 4.4 cm. compared to approximately 4.5 to 5.0 cm. for the 'BFP-721 Bright Lilac' cultivar.

*Form.*—Both the 'BFP-864 Bright Lavender' cultivar and the 'BFP-721 Bright Lilac' cultivar are semi-double with petaloids.

*Number of petals.*—Commonly forms approximately 6 to 10 petals per floret whereas the 'BFP-721 Bright Lilac' cultivar commonly possess as approximately 6 to 7 petals per floret.

*Number of petaloids.*—Commonly forms approximately 1 petaloid per floret whereas the 'BFP-721 Bright Lilac' cultivar commonly forms approximately 1 to 2 petaloids per floret.

*Color.*—General tonality from a distance of three meters: Lavender. Adaxial: Red-Purple Group 74A commonly with white coloration that radiates outwardly from the bases of the petals. This compares to Red-Purple Group 74B with a white eye on the upper two petals for the 'BFP-721 Bright Lilac' cultivar. Abaxial: Red-Purple Group 73B with veins of Red-Purple Group 74A. This compares to Red-Purple Group 73A with veins of Red-Purple Group 74B for the 'BFP-721 Bright Lilac' cultivar.

C. Bud:

*Shape.*—Oval-rounded.

*Color.*—Adaxial: Red-Purple Group 74A compared to Red-Purple Group 74B for the 'BFP-721 Bright Lilac' cultivar. Abaxial: Red-Purole Group 73B compared to Red-purple Group 73A for the 'BFP-721 Bright Lilac' cultivar.

D. Reproductive organs:

*Androecium.*—The anthers are commonly approximately 2 mm. in length. The pollen color commonly is Orange-Red Group 31A for both the 'BFP-864 Bright Lavender' cultivar and the 'BFP-721 Bright Lilac' cultivar. The filaments are approximately 4 to 7 mm. in length.

*Gynoecium.*—The pistil lenth commonly is approximately 9.0 mm. There is a single stigma which commonly has a length of approximately 4.0 mm. which commonly branches into 5 parts, and the style length is approximately 5.0 mm.

*Fertility.*—Commonly does not produce fruits in the absence of mechanical fertilization.

E. Spring flowering response period: Approximately 6 to 7 weeks from rooted cuttings under standard greenhouse conditions.

F. Outdoor flower production: Freely flowering under outdoor growing conditions with substantially continuous blooming.

G. Durability: Ships well.

Plant

A. Foliage: Medium green.

*Form.*—Reniform, with cordate base.

*Margin.*—Crenate.

*Color.*—Adaxial: Green Group 137A for both the 'BFP-864 Bright Lavender' cultivar and the 'BFP-721 Bright Lilac' cultivar. Abaxial: Green Group 137C for both the 'BFP-864 Bright Lavender' cultivar and the 'BFP-721 Bright Lilac' cultivar.

*Size.*—Approximately 9.0 to 10.0 cm. at the widest point and approximately 7.6 to 8.5 cm. at the narrowest point. This compares to approximately 8.0 to 9.0 cm. at the widest point and approximately 7.0 to 7.5 cm. at the narrowest point for the 'BFP-721 Bright Lilac' cultivar.

*Tolerance to Botrytis.*—Some under field growing conditions.

B. General appearance and form:

*Internode length.*—Commonly varies from approximately 1.0 to 2.0 cm. This compares to approimately 1.0 to 1.5 cm. for the 'BFP-721 Bright Lilac' cultivar.

*Branching pattern.*—Freely basal branching. No pinching is required to obtain self-branching. A vigorous self-branching growth habit is observed in the absence of a growth regulator.

*Height.*—Approximately 27 to 33 cm. above a 10 cm. pot at 9 weeks under standard greenhouse conditions. This compares to approximately 26 to 28 cm. for the 'BFP-721 Bright Lilac' cultivar.

I claim:

1. A new and distinct Geranium cultivar named 'BFP-864 Bright Lavender', substantially as herein shown and described, which:

(a) exhibits attractive semi-double lavender florets commonly with white coloration that radiates outwardly from the bases of the petals, (b) forms medium green foliage, and (c) exhibits a medium self-branching growth habit in the absence of a growth regulator.

* * * * *